(12) United States Patent
Almqvist et al.

(10) Patent No.: US 9,505,689 B2
(45) Date of Patent: Nov. 29, 2016

(54) PROCESS AND REACTION SYSTEM FOR THE PREPARATION OF METHANOL

(71) Applicant: Haldor Topsøe A/S, Kgs. Lyngby (DK)

(72) Inventors: Marcus Almqvist, Malmö (SE); Christophe Duwig, Malmö (SE); Per Juul Dahl, Vedbæk (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/414,944

(22) PCT Filed: Nov. 19, 2012

(86) PCT No.: PCT/EP2012/072957
§ 371 (c)(1),
(2) Date: Jan. 15, 2015

(87) PCT Pub. No.: WO2014/012601
PCT Pub. Date: Jan. 23, 2014

(65) Prior Publication Data
US 2015/0175509 A1    Jun. 25, 2015

(30) Foreign Application Priority Data

Jul. 18, 2012    (DK) ................................ 2012 70439

(51) Int. Cl.
*C07C 29/151*    (2006.01)
*C07C 29/141*    (2006.01)
*C07C 29/152*    (2006.01)
*B01J 19/24*    (2006.01)

(52) U.S. Cl.
CPC .......... *C07C 29/141* (2013.01); *B01J 19/2445* (2013.01); *C07C 29/152* (2013.01); *B01J 2219/00051* (2013.01); *B01J 2219/24* (2013.01)

(58) Field of Classification Search
CPC . C07C 29/141; C07C 29/1516; C07C 31/04; B01J 19/2445; B01J 2219/00051; B01J 2219/24; C01C 1/0405
See application file for complete search history.

(56) References Cited

U.S. PATENT DOCUMENTS

| 5,631,302 A | 5/1997 | König et al. |
| 7,786,180 B2 * | 8/2010 | Fitzpatrick ........ C07C 29/1518 518/700 |
| 7,790,775 B2 | 9/2010 | Early |

* cited by examiner

*Primary Examiner* — Jafar Parsa
*Assistant Examiner* — Medhanit Bahta
(74) *Attorney, Agent, or Firm* — Blank Rome LLP

(57) ABSTRACT

Process and reaction system for the preparation of methanol comprising two reaction units, wherein a first unit is operated on a mixture of fresh synthesis gas and unconverted synthesis gas and a second unit solely with unconverted synthesis gas.

4 Claims, 2 Drawing Sheets

… (1)

PROCESS AND REACTION SYSTEM FOR THE PREPARATION OF METHANOL

Figure 1:
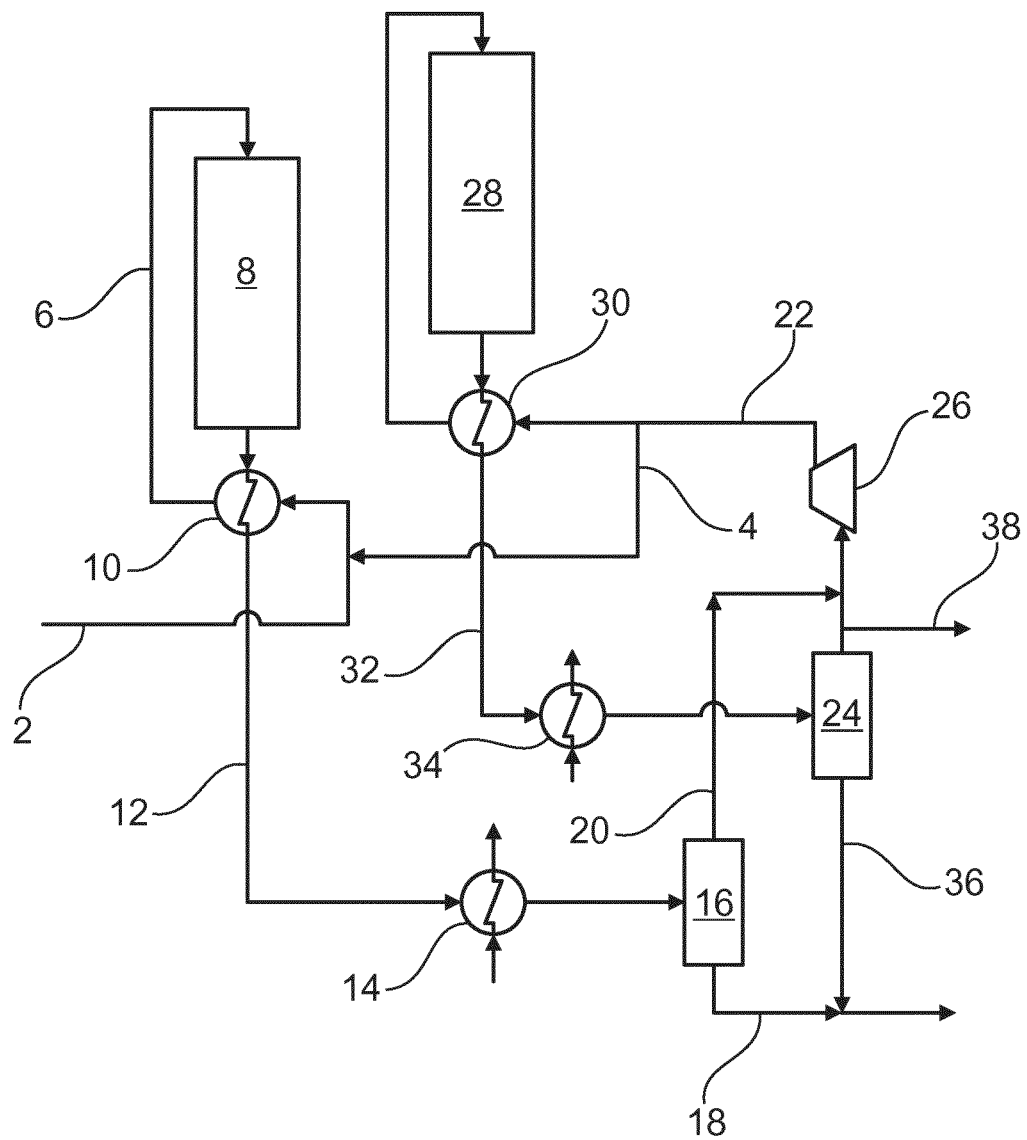

The present invention relates to a process for the preparation of methanol by catalytic conversion of methanol synthesis gas and a reaction system for use in the process. More particularly, methanol is by the invention prepared in two reaction units, in which a first unit is operated on fresh synthesis gas mixed with unconverted synthesis gas separated from a methanol reactor effluent and in which a second reaction unit is operated on unconverted synthesis gas as the sole feedstock.

It is well known in the art that a synthesis gas derived from natural gas or heavier hydrocarbons and coal is highly reactive for direct methanol synthesis and harmful for the methanol catalyst. Additionally use of such high reactive synthesis gas results in formation of large amounts of by-products.

The reaction of carbon oxides and hydrogen to methanol is equilibrium limited and conversion of the synthesis gas to methanol per pass through a methanol catalyst is relatively low, even when using a high reactive synthesis gas.

Because of the low methanol production yield in a oncethrough methanol conversion process, the general practice in the art is to recycle unconverted synthesis gas separated from the reaction effluent and dilute the fresh synthesis gas with the recycle gas.

This typically results in the so-called methanol synthesis loop with one or more reactors connected in series being operated on fresh synthesis gas diluted with either recycled unconverted gas separated from the reactor effluents or on the reactor effluent containing methanol and unconverted synthesis gas. The recycle ratio (recycle gas:fresh synthesis feed gas) is 2:1 up to 7:1 in normal practice.

Serial synthesis of methanol in two reactors is disclosed in U.S. Pat. No. 5,827,901, wherein fresh synthesis gas admixed with recycled unconverted synthesis gas is converted in a first reactor and the entire effluent form the first reactor is further converted in a second rector.

U.S. Pat. No. 6,433,029 describes a methanol synthesis loop with two methanol reactors in series, in which a first reactor is operated on fresh synthesis gas diluted with unconverted synthesis gas and a second reactor with the effluent from the first reactor optionally admixed with fresh synthesis gas.

Synthesis of methanol in two reactors being connected in parallel is inter alia disclosed in U.S. Pat. No. 5,631,302. Methanol is in this process layout performed in a first reactor with fresh methanol synthesis gas and in a second reactor with unconverted synthesis gas separated from the product effluent from the first and second reactor.

By the present invention methanol synthesis is performed in two parallel reaction units, in which the first unit is operated on fresh synthesis gas adjusted with recycled unconverted synthesis gas and the second unit solely on recycled unconverted synthesis gas.

The main principle of the invention is, thus, to provide the highest possible catalyst performance at an acceptable low formation of by-products in the first reaction unit, and to ensure overall high synthesis gas conversion efficiency by means of the second reaction unit. This results in a reduced overall catalyst volume and lower equipment costs especially for large capacity plant where the synthesis in any case must be performed in two or more reactors.

Accordingly, this invention is a process for the preparation of methanol comprising the steps of (a) providing a fresh methanol synthesis gas containing hydrogen, carbon monoxide and carbon dioxide;

(b) providing a recycle gas stream containing unconverted methanol synthesis gas and mixing a part of the recycle stream with the fresh synthesis gas to a process gas stream;

(c) introducing and reacting the process gas stream in a first methanol reaction unit in presence of a methanol catalyst and obtaining a first effluent stream containing methanol and a part of the unconverted synthesis gas contained in the recycle stream; and (d) introducing and reacting at least another part of the recycle gas stream in a second methanol reaction unit in presence of a methanol catalyst and obtaining a second effluent stream containing methanol and another part of the unconverted synthesis gas contained in the recycle stream, wherein the recycle stream is pressurised by a common circulator.

A methanol process with parallel operated reactors and an out recycle and inner recycle loop is disclosed in U.S. Pat. No. 7,790,775. The inner recycle loop with unconverted methanol synthesis gas from a first methanol reactor provides in this process the feedstock for a second reactor. The first reactor is operated on unconverted synthesis gas recovered from the effluent of the second reactor, which is recycled to the first reactor in the outer recycle loop. The recycled synthesis gas is admixed with fresh synthesis gas prior to introduction into the first reactor.

In contrast to the process layout of the above U.S. patent, the process according to the invention employs unconverted synthesis gas collected from both the first and second reaction unit. Thus the recycle gas to both the first and second unit can be pressurised and circulated by a common circulator. Compared to the process of U.S. Pat. No. 7,790,775, the pressure loss in the recirculation stream is in the process according to the invention advantageously considerable lower because the inventive process layout ensures that the two reaction units operate at the same pressure, that is the circulator outlet pressure, whereas the first reactor in U.S. Pat. No. 7,790,775 must be operated at the circulator pressure minus the pressure loss in the inner loop.

In a specific embodiment of the invention, the unconverted synthesis gas is in the first and second effluent stream separated from methanol by cooling and condensing the methanol in each effluent stream separately or by combining the first or second effluent stream prior to the cooling and condensing the methanol.

In further an embodiment of the invention, the recycle stream is obtained by (i) cooling the first effluent stream from the first methanol reaction unit and separating the methanol contained in the first effluent from the unconverted synthesis;

(ii) cooling the second effluent stream from the second methanol reaction unit and separating the methanol contained in the second effluent stream from the unconverted synthesis gas; and (iii) combining the unconverted synthesis gas separated from the first and second effluent stream to the recycle stream.

In still an embodiment, the recycle stream is obtained by (i) mixing the first effluent stream from the first methanol reaction unit with the second effluent stream from the second methanol reaction unit;

(ii) cooling the mixed effluent stream and separating the unconverted synthesis gas from the methanol contained in the mixed first and second effluent stream.

The first and second methanol reaction unit can comprise one or more reactors selected from boiling water cooled reactors, gas cooled reactors, quench reactors and adiabatic operated reactors, connected in series and/or in parallel.

The term "methanol catalyst" used hereinbefore and in the following refers to any catalyst being active in the conversion of hydrogen, carbon monoxide and carbon dioxide to methanol. Those catalysts are not part of the invention and are extensively disclosed in the patent literature.

Appropriate methanol catalysts for use in the invention are as an example the known copper-zinc based catalysts.

The invention provides furthermore a reaction system for use in a process for the preparation of methanol, the system comprises a first and second methanol reaction unit containing each a methanol catalyst;

a process gas stream passageway for introducing a process gas stream of a fresh synthesis gas mixed with an unconverted synthesis gas into the first methanol reaction unit and a passageway for introducing a recycle stream of unconverted synthesis gas into the second methanol reaction unit;

a first effluent passageway for withdrawing a first methanol containing effluent stream from the first reaction unit and a second effluent passageway for withdrawing a second methanol containing effluent from the second reaction unit; separating means for separating methanol from unconverted synthesis gas contained in the first and second effluent stream;

a circulation passageway for circulating the unconverted synthesis gas to the second methanol reaction unit;

a split stream passageway for passing a part of the unconverted synthesis gas from the circulation passageway to the process gas stream passageway; and a circulator arranged in the circulation passageway between the separating means and the split stream passageway for circulating the unconverted synthesis gas.

In a specific embodiment of the reaction system according to the invention, each of the first effluent and second effluent passageway are provided with cooling means for cooling the first and second effluent stream and wherein each of the passageways are separately connected downstream of the cooling means to the separating means.

In a further embodiment, the second effluent passageway is connected to the first effluent passageway at a connecting point upstream of the separating means and wherein the cooling means are arranged in the passageways downstream of the connecting point.

The first and second reaction unit in the above embodiments can comprise one or more methanol reactors selected from boiling water cooled reactors, gas cooled reactors, quench reactors and adiabatic operated reactors connected in series and/or in parallel.

Figure 2:
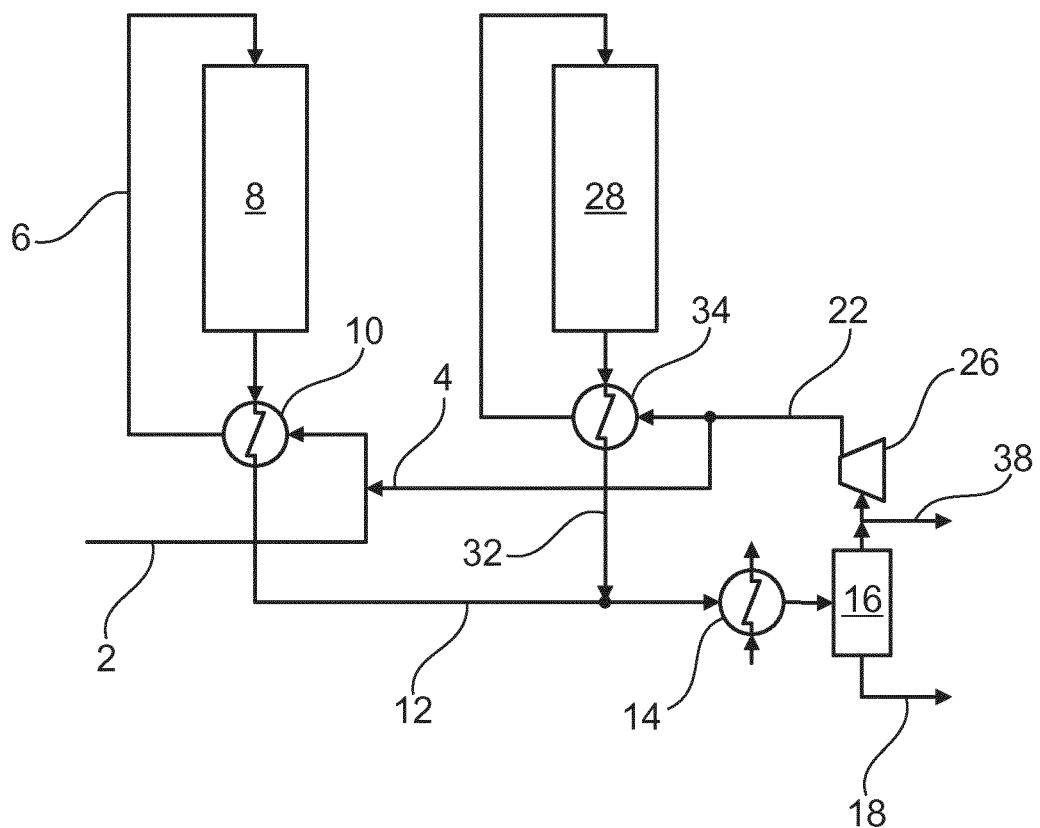

The invention is explained in more detail in the following description by reference to the drawings in which FIG. 1 is simplified flow sheet showing a process of the invention wherein the reactor effluents are cooled and unconverted synthesis gas is separated from methanol in separate cooling and separating units; and FIG. 2 shows a simplified flow sheet according to another specific embodiment, in which the first and second reactor effluents are combined prior to cooling and separation in a common cooler and separator.

Referring to FIG. 1, a feed gas stream 2 of fresh methanol synthesis gas is combined with unconverted synthesis gas circulated in line 4 to a process gas stream 6. Before being introduced into a first methanol reaction unit 8, the process gas stream is preheated in a feed/effluent heat exchanger 10 by heat contained in a first effluent stream 12 withdrawn from reaction unit 8. Effluent stream 12 contains methanol formed trough reaction of hydrogen with carbon monoxide and dioxide contained in the process gas stream according to the known reaction scheme when the gas stream comes in contact with a methanol catalyst arranged in one or more reactors (not shown) in reaction unit 8. Because of the above mentioned equilibrium limitations, effluent stream 12 further contains unconverted synthesis gas. By passage through feed/effluent heat exchanger 10, the effluent stream is cooled. The stream is further cooled in cooler 14 to condense the amounts of methanol in the effluent stream. Condensed methanol is separated from unconverted synthesis gas in the thus cooled effluent stream 12 in a separator 16 and withdrawn through product line 18. The unconverted synthesis gas separated in separator 16 is passed through line 20 to recirculation line 22 and mixed with further amounts of unconverted synthesis gas from a second separator 24. The combined amounts of unconverted synthesis gas are pressurised and circulated by means of a circulator 26 arranged in line 22. A part of the compressed unconverted synthesis gas is passed as split stream through line 4 to the fresh synthesis gas in line 2. The remaining amounts of the gas are introduced into a second methanol reaction unit 28. Before being introduced into unit 28 the gas is preheated in feed/effluent heat exchanger 30 with a second effluent stream 32 from reaction unit 28. Effluent stream 32 contains methanol formed by reaction of the unconverted synthesis gas in contact with a methanol catalyst in the same manner as described above. Like unit 8, unit 28 can comprise one or more separate methanol reactors, connected in series and/or in parallel.

The second effluent stream 32 is partly cooled in heat exchanger 30 and in cooler 34 to condense methanol contained in the effluent stream. The condensed amounts of methanol are subsequently separated in separator 24 from unconverted synthesis gas further contained in effluent stream 32. The separated amounts of methanol are withdrawn from separator 24 in line 36 and combined in product line 18 with the amounts of methanol separated in separator 16. A part of the unconverted synthesis gas in line 22 is purged through line 38 in order to prevent build-up of inerts.

The process layout shown in FIG. 2 is similar to that shown in FIG. 2, with the exception that effluent 14 from the first reaction unit 8 is combined with the second effluent from reaction unit 28 before being cooled and separated in a common cooler 14 and separator 16. The combined amounts of unconverted synthesis from the first 12 and second effluent stream 32 are separated from methanol being withdrawn through product line 18. The separated unconverted synthesis gas in line 22 is pressurised and circulated by means of circulator 26 arranged in line 22. Prior to pressurizing in circulator 26, a part of the unconverted synthesis gas in line 22 is purged though line 38. The unconverted synthesis gas in line 22 is preheated in feed/effluent heat exchanger 34 and then passed to reaction unit 28. A part of the unconverted synthesis gas split from line 22 is passed in line 4 to line 2 and combined with fresh synthesis gas to form process gas stream 6. The process gas stream is preheated in feed/effluent heat exchanger 10 before being introduced and reacted in methanol reaction unit 8. The remaining amounts of unconverted synthesis gas in line 22 are preheated in feed/effluent heat exchanger 34 and introduced into and reacted in reaction unit 28.

The invention claimed is:

1. Process for the preparation of methanol comprising the steps of (a) providing a fresh methanol synthesis gas containing hydrogen, carbon monoxide and carbon dioxide;

(b) providing a recycle gas stream containing unconverted methanol synthesis gas from a first reaction unit and a second methanol reaction unit, wherein the recycle stream is pressurized by a common circulator, and mixing a part of the recycle stream with the fresh synthesis gas to form a process gas stream;

(c) introducing and reacting the process gas stream from (b) in the first methanol reaction unit in presence of a methanol catalyst and obtaining a first effluent stream containing methanol and a part of the unconverted synthesis gas contained in the recycle stream; and (d) introducing and reacting at least another part of the recycle gas stream in the second methanol reaction unit in presence of a methanol catalyst and obtaining a second effluent stream containing methanol and another part of the unconverted synthesis gas contained in the recycle stream.

2. The process of claim 1, wherein the unconverted synthesis gas in the first and second effluent stream is separated from the methanol by cooling and condensing methanol in each effluent stream separately or by combining the first or second effluent stream prior to the cooling and condensing methanol.

3. The process of claim 1, wherein the recycle stream is obtained by
   (i) cooling the first effluent stream from the first methanol reaction unit and separating the methanol contained in the first effluent from the unconverted synthesis;
   (ii) cooling the second effluent stream from the second methanol reaction unit and separating the methanol contained in the second effluent stream from the unconverted synthesis gas; and
   (iii) combining the unconverted synthesis gas separated from the first and second effluent stream to the recycle stream.

4. The process of claim 1, wherein the recycle stream is obtained by
   (i) mixing the first effluent stream from the first methanol reaction unit with the second effluent stream from the second methanol reaction unit;
   (ii) cooling the mixed effluent stream and separating the unconverted synthesis gas from the methanol contained in the mixed first and second effluent stream.

\* \* \* \* \*